United States Patent
Arie et al.

(10) Patent No.: US 10,264,796 B2
(45) Date of Patent: Apr. 23, 2019

(54) METHOD FOR PRODUCING SEEDS OF PLANTS RESISTANT TO SEEDLING DISEASES, AND METHOD FOR PREVENTING THE ONSET OF AND CONTROLLING SEEDLING DISEASES

(71) Applicant: National University Corporation, Tokyo University of Agriculture and Technology, Tokyo (JP)

(72) Inventors: Tsutomu Arie, Tokyo (JP); Tohru Teraoka, Tokyo (JP); Youko Nonaka, Tokyo (JP); Akihiro Kato, Tokyo (JP); Jun Tanaka, Tokyo (JP); Tomomi Tokunaga, Tokyo (JP); Kenichi Kurauchi, Kuroishi (JP); Tomotaka Suzuki, Osaki (JP)

(73) Assignee: NATIONAL UNIVERSITY CORPORATION TOKYO UNIVERSITY OF AGRICULTURE AND TECHNOLOGY, Tokyo (JP)

( * ) Notice: Subject to any disclaimer, the term of this patent is extended or adjusted under 35 U.S.C. 154(b) by 638 days.

(21) Appl. No.: 14/773,026

(22) PCT Filed: Mar. 7, 2014

(86) PCT No.: PCT/JP2014/056059
§ 371 (c)(1),
(2) Date: Sep. 4, 2015

(87) PCT Pub. No.: WO2014/136967
PCT Pub. Date: Sep. 12, 2014

(65) Prior Publication Data
US 2016/0015040 A1    Jan. 21, 2016

(30) Foreign Application Priority Data
Mar. 8, 2013    (JP) ................................. 2013-047121

(51) Int. Cl.
| | | |
|---|---|---|
| *A01N 63/04* | (2006.01) |
| *A01N 25/00* | (2006.01) |
| *C12N 1/14* | (2006.01) |
| *A01H 5/00* | (2018.01) |
| *A01H 5/10* | (2018.01) |

(52) U.S. Cl.
CPC ............. *A01N 63/04* (2013.01); *A01N 25/00* (2013.01); *C12N 1/14* (2013.01); *A01H 5/00* (2013.01); *A01H 5/10* (2013.01)

(58) Field of Classification Search
None
See application file for complete search history.

(56) References Cited

U.S. PATENT DOCUMENTS

| | | | | |
|---|---|---|---|---|
| 6,004,774 A * | 12/1999 | Marrone | ................ | A01N 63/00 424/115 |
| 2007/0093387 A1* | 4/2007 | Sumi | ..................... | A01N 63/00 504/100 |
| 2015/0335029 A1* | 11/2015 | Mitter | ..................... | A01H 3/00 504/117 |

FOREIGN PATENT DOCUMENTS

| | | |
|---|---|---|
| JP | 2001-346407 A | 12/2001 |
| JP | 2003-192515 A | 7/2003 |

OTHER PUBLICATIONS

Singh et al., Environment & Ecology, 2012, 30:834-837.*
Chiochetti et al., Plant Disease, 1999, vol. 83 No. 6, pp. 576-581.*
Janusz et al., Enzyme and Microbial Technology 52:1-12, available online in Oct. 2012. (Year: 2012).*
PCT International Search Report dated Jun. 3, 2014, issued in a related PCT application No. PCT/JP2014/056059 (2 pgs.).

* cited by examiner

*Primary Examiner* — Jennifer Pitrak McDonald
*Assistant Examiner* — Qing Xu
(74) *Attorney, Agent, or Firm* — Lucas & Mercanti, LLP

(57) ABSTRACT

A method for producing a seed of a plant resistant to seedling diseases is provided which includes contacting a non-pathogenic microbe corresponding to a seed-borne pathogen with a flower part of a host plant around the flowering time and collecting a seed of the host plant colonized by the non-pathogenic microbe obtained thereafter, and a method for controlling seedling diseases using the seed.

4 Claims, No Drawings
Specification includes a Sequence Listing.

METHOD FOR PRODUCING SEEDS OF PLANTS RESISTANT TO SEEDLING DISEASES, AND METHOD FOR PREVENTING THE ONSET OF AND CONTROLLING SEEDLING DISEASES

CROSS-REFERENCE TO RELATED APPLICATIONS

This application is a 371 of PCT/JP2014/056059, filed Mar. 7, 2014, which claims the benefit of Japanese Patent Application No. 2013-047121, filed Mar. 8, 2013.

TECHNICAL FIELD

The present invention relates to a method for producing plant seeds resistant to seedling diseases using a non-pathogenic microbe corresponding to a seed-borne pathogen, and a technique for preventing the onset of and controlling seedling diseases in the next generation using the plant seeds resistant to the diseases.

BACKGROUND ART

Seed-borne diseases of plants are, together with soil-borne diseases, ranked among seedling diseases. A seed-borne pathogen causing the seed-borne diseases is often transmitted to the next generation via seeds carrying the pathogen and spread by infecting seedling plants in the next generation.

For example, rice bakanae disease is an agriculturally important seed-borne disease of rice caused by the rice bakanae disease fungus belonging to *Fusarium fujikuroi* (perfect stage name: *Gibberella fujikuroi*). The germination of rice seeds (seed paddies) colonized by the rice bakanae disease fungus results in not only that the pathogenic fungus is transmitted to surrounding healthy rice seedlings but also that the infected plants exhibit abnormal spindly growth and yellowing symptoms and afterwards withers. In the withered plants, many conidia of the fungus are formed on the surface of the lower leaf sheath, and the conidia fly apart and adhere to the flower part, pistils, anthers, and anther corpses of surrounding healthy stocks to pollute paddies. The paddies each provide a source of infection in the next year as a seed carrying the fungus (Non Patent Literature 1).

This disease can be effectively controlled by seed disinfection using chemical pesticides such as benomyl and pefurazoate, and has therefore been calmed down in fields for a long time. However, there has been concern that these agents are invalidated since excessive dependence on chemical pesticides hastens the appearance of resistant strains. In addition, the use of a fungicide having a different mechanism such as ipconazole has calmed down the disease. However, the use of chemical pesticides always holds the risk of the appearance of resistant fungi and also has problems, such as environment pollution and remaining in rice. With the current increased concern about environment, there is a need for shifting to environmentally sound and sustainable agriculture, and for example, a physical control method, such as a hot water soaking method, and a biological control method using a microbial pesticide are beginning to be spread as an alternative control technique for chemical pesticides. These methods each take aim at giving a safe feeling to consumers by producing safe agricultural products, reducing an environmental load by plant protection, and controlling pests against which chemical pesticides cannot hardly be used.

Meanwhile, however, the effects of conventional physical control and biological control methods are unstable compared to chemical pesticides and they have the problem of not being capable of sufficiently suppress the occurrence of seed-borne diseases including rice bakanae disease and the problem of resulting in increased labor force associated with treatment. In addition, the microbial pesticide has a problem in terms of cost, and the physical control method has problems, such as complicated treatment and reduced seed germination rate.

PRIOR ART DOCUMENT

Non-Patent Document

Non-Patent Document 1: Sakumotsu Byogai Jiten (Crop Disease Dictionary), edited by Kunihei Kishi, Zenkoku Nosonkyoiku Kyokai (The National Rural Education Association of Japan)

SUMMARY OF THE INVENTION

Problem to be Solved by the Invention

Objects of the present invention are: to develop a biological control agent microbe which can be supplied inexpensively with safety and has a high effect of controlling seedling diseases including seed-borne diseases and soil-borne diseases; to provide a microbial pesticide using the microbe as an active ingredient; and to establish a method for effectively treating said microbial pesticide and effectively controlling seedling diseases; in order to provide a technique which can reduce cultivator's labor and cost and enables stably cultivating safe agricultural products, for the stable production and supply of foods.

Means for Solving the Problem

As described above, a big problem of the biological control method using a microbial pesticide is that its effect is not stable. One of the causes thereof is that it is difficult for a microbe as an active ingredient to colonize in a plant body or in the tissues, rhizosphere, and the like for a period until the microbe exerts a control effect.

The present inventors have conceived a technique to exploit a biological control capability against seedling diseases by producing a seed colonized by a non-pathogenic microbe in advance by applying the non-pathogenic microbe corresponding to a seed-borne pathogen and having colonizing ability in plants using a method such as spraying on a flower part of a host plant at the flowering time, thereby allowing the non-pathogenic microbe to be colonized in the plant body in the next generation. As a result of experiment, it has been found that the plant body such as a seedling in the next generation can be occupied by the non-pathogenic microbe and/or acquires resistance to the pathogen so that the occurrence of seedling diseases including soil-borne diseases as well as seed-borne diseases is effectively suppressed. The present invention is based on the above findings and provides the following.

(1) A method for producing seeds of a plant resistant to seedling diseases, comprising a step of contacting a non-pathogenic microbe corresponding to a seed-borne pathogen with a flower part of a host plant around the flowering time, and a step of collecting seeds of the host plant colonized by the non-pathogenic microbe, obtained after the above step.

(2) The production method according to (1), wherein the host plant is a gramineous plant.

(3) The production method according to (2), wherein the gramineous plant is rice.

(4) The production method according to any of (1) to (3), wherein the non-pathogenic microbe is selected from the group consisting of fungi of the genus *Fusarium*, the genus *Nectria*, the genus *Gibberella*, the genus *Calonectria*, the genus *Hypomyces*, the genus *Trichoderma*, the genus *Penicillium*, the genus *Talaromyces*, the genus *Acremonium*, the genus *Alternaria*, and the genus *Verticillium* and bacteria of the genus *Bacillus*, the genus *Pseudomonas*, the genus *Xanthomonas*, and the genus *Streptomyces*.

(5) The production method according to any of (1) to (3), wherein the non-pathogenic microbe is a fungus of the genus *Fusarium* selected from the group consisting of *Fusarium oxysporum, Fusarium moniliforme, Fusarium fujikuroi, Fusarium proliferatum*, and *Fusarium sacchari*.

(6) The production method according to any of (1) to (3), wherein the non-pathogenic microbe is of Accession Number NITE BP-01538 or NITE BP-01539.

(7) A seed of a plant resistant to seedling diseases obtained by contacting a non-pathogenic microbe corresponding to a seed-borne pathogen with a flower part of a host plant around the flowering time.

(8) The seed according to (7), wherein the host plant is a gramineous plant.

(9) The seed according to (7) or (8), wherein the non-pathogenic microbe is the non-pathogenic microbe as defined in any of (4) to (6).

(10) A method for preventing the onset of and controlling seedling diseases using the seed of the plant resistant to seedling diseases according to (7) or (8).

(11) The prevention and control method according to (10), wherein the plant is a gramineous plant.

(12) The prevention and control method according to (10) or (11), wherein the seedling diseases are seed-borne diseases and soil-borne diseases.

(13) A microbial pesticide for controlling seedling diseases comprising a non-pathogenic microbe corresponding to a seed-borne pathogen as an active ingredient.

(14) The microbial pesticide according to (13), wherein the microbial pesticide is for applying to a gramineous plant.

(15) The microbial pesticide according to (13) or (14), wherein the non-pathogenic microbe is the non-pathogenic microbe as defined in any of (4) to (6).

The contents of the specification and/or drawings of JP Patent Application No. 2013-047121, to which the present application claims the priority are incorporated herein.

Effects of Invention

The seed of a plant resistant to seedling diseases according to the present invention enables the production and provision of seedling individual (seedling) resistant to seedling diseases.

By the method for producing seeds of a plant resistant to seedling diseases according to the present invention, seeds of a plant resistant to seedling diseases can be simply and efficiently produced.

By the method for preventing the onset of and controlling seedling diseases according to the present invention, the onset of seedling diseases can be prevented and controlled.

The microbial pesticide for controlling seedling diseases according to the present invention enables the provision of an inexpensive and highly efficient microbial pesticide for efficiently preventing and controlling seedling diseases.

MODE FOR CARRYING OUT THE INVENTION

1. Method for Producing Seed(s) of a Plant Resistant to Seedling Diseases

A first aspect of the present invention relates to a method for producing seed(s) of a plant resistant to seedling diseases (herein often referred to as the "production method"). The production method of the present invention enables the production of plant seed(s) having acquired disease resistance like a cultivar resistant to seedling diseases by utilizing a biological control agent microbe, and the provision of the plant seed.

1-1. Definition

The terms used herein shall be defined as follows.

The "Seedling disease" is a plant disease transmitted or occurring during the seedling raising period, and includes seed-borne diseases and soil-borne diseases.

The "Seed-borne disease" is a plant disease occurring due to infection with a seed-borne pathogen and is a disease transmitted to a relevant plant stock as well as surrounding stocks through, for example, a seed colonized by the seed-borne pathogen during seed soaking or germination. On the other hand, the "soil-borne disease" is a plant disease occurring due to infection with a pathogen originally surviving in the soil.

"Seed-borne pathogen" refers to a microbe which colonizes in a seed after infecting a flower part formed in a host plant and causes disease symptoms in a seedling individual. As used herein, the "seedling individual" refers to a seedling having sprouted from a seed or a plant individual having resulted from its growth. As used herein, the "microbe" generally refers to a microscopic organism which is difficult to be recognized visually, for example, bacteria and fungi. Fungi are in a eukaryote group belonging to the Kingdom of Fungi in terms of biological classification, and sometimes called true fungi or filamentous fungi. Fungi include unicellular eukaryotic microbes, such as yeast, or multicellular eukaryotic microbes, such as filamentous fungi which are relatively difficult to be recognized visually (including mold) and mushrooms.

As described above, seed-borne pathogens are a group having pathogenicity, falling within certain microbial species. Examples of microbes encompassing seed-borne pathogens include bacteria of the genus *Bacillus*, the genus *Pseudomonas* (including now bacteria of the genus *Burkholderia* and the genus *Acidovorax*), the genus *Xanthomonas*, and the genus *Streptomyces*, and fungi of the genus *Fusarium*, the genus *Nectria*, the genus *Gibberella*, the genus *Calonectria*, the genus *Hypomyces*, the genus *Trichoderma*, the genus *Penicillium*, the genus *Talaromyces*, the genus *Acremonium*, the genus *Alternaria*, and the genus *Verticillium*. Examples of fungi of the genus *Fusarium* include *F. oxysporum, F. moniliforme, F. fujikuroi, F. proliferatum*, and *F. sacchari*. The genus *Fusarium* is the major name of the imperfect stage of the genus *Gibberella*, and the genus *Gibberella* is herein a synonym of the genus *Fusarium*. The route and time of infection of a host plant with a seed-borne pathogen vary slightly depending on the type thereof, but the pathogen typically infects the flower part of the host plant in the flower season and then colonizes in a seed and/or an ovary (a caryopsis for a gramineous plant). The seed-borne pathogen colonizes in the plant tissue, rhizosphere, and the like during the germination of the seed carrying the pathogen and the growth of a seedling individual and is further transmitted to surrounding healthy stocks and proliferate, resulting in the onset of the seed-borne disease specific to the strain of the pathogen. Specific examples of seed-borne diseases include rice bakanae disease (due to *Gibberella fujikuroi*), rice blast (due to *Magnaporthe oryzae*), damping-off (due to a fungus of the genus *Fusarium*, the genus *Pythium*, the genus *Rhizoctonia*, or the genus *Trichoderma*), Helminthosporium blight (due to *Cochliobolus miyabeanus*), bacterial seedling blight (due to *Pseudomonas plantarii* (now *Burkholderia plantarii*)), glume blight (due to *Pseudomonas glumae* (now *Burkholderia glumae*)), and bacterial brown stripe (due to *Pseudomonas avenae* (now *Acidovorax avenae*)).

Angiosperms and gymnosperms fall under a host plant for seed-borne pathogens. The angiosperm may be a dicotyledon or a monocotyledon. Examples of the monocotyledon include a gramineous (Poaceae) plant. Examples of the dicotyledon include a rosaceous (Rosaceae) plant, a solanaceous (Solanaceae) plant, a leguminous (Fabaceae) plant, a cucurbitaceous (Cucurbitaceae) plant, and a cruciferous (Brassicaceae) plant. Preferred is a gramineous plant. Examples of the gramineous plant herein include agriculturally important species such as rice (*Oryza sativa* and *O. glaberrima*), wheat (*Triticum aestivum, T. compactum*, and *T. durum*), barley (*Hordeum vulgare*), rye (*Secale cereale*), millet (*Panicum miliaceum*), foxtail millet (*Setaria italica*), Japanese millet (*Echinochloa esculenta*), sorghum (*Sorghum bicolor*), corn (*Zea mays*), and sugar cane (*Saccharum officinarum*). Preferred are rice, wheat, barley, corn, and sugar cane, more preferably rice.

The "biological control agent microbe" has the same meaning as the "non-pathogenic microbe corresponding to a seed-borne pathogen" herein. The "corresponding" as used here means mainly belonging to the same species or the same genus, or being close to each other taxonomically, or having a biological control effect. Thus, the "non-pathogenic microbe corresponding to a seed-borne pathogen" refers to a group in a certain microbial species not having pathogenicity despite belonging to the same species as a seed-borne pathogen taxonomically. For example, non-pathogenic fungi of the genus *Fusarium*, e.g., *F. oxysporum* and *F. fujikuroi* fall under a non-pathogenic fungus corresponding to a rice bakanae disease fungus. The biological control agent microbe has a feature of not causing disease symptoms in a host plant while retaining high infectivity to and colonizing ability in a host plant. The host plant colonized by the biological control agent microbe becomes resistant to general seedling diseases including not only seed-borne diseases but also soil-borne diseases. Specific examples of the biological control agent microbe include *Fusarium oxysporum* non-pathogenic strain W3 (Accession Number: NITE BP-01538) or *Fusarium oxysporum* non-pathogenic strain W5 (Accession Number: NITE BP-01539). These biological control agent microbes were originally deposited on Feb. 13, 2013 in the Patent Microorganisms Depositary, National Institute of Technology and Evaluation (#122, 2-5-8 Kazusakamatari, Kisarazu-shi, Chiba 292-0818, Japan) in Japan.

The "plant resistant to seedling diseases" refers to a plant colonized by a biological control agent microbe, which exhibits resistance to general seedling diseases including seed-borne diseases and soil-borne diseases and does not show clear symptoms of these diseases.

1-2. Method for Separating Biological Control Agent Microbe

A method for separating the biological control agent microbe used in the invention described herein will be described. As described above, the biological control agent microbe can be relatively easily separated from a plant body since the microbe is widely present in nature. For example, see a method as described in Tateishi H. & Chida T. 2000, J. Gen. Plant Pathol., 66: 353-359.

(1) Separation Source

A separation source of the biological control agent microbe may be a plant tissue (leaf, hypocotyl, leaf sheath, leaf stalk, stem, flower organ, fruit, root, or the like) of a healthy conspecific stock growing around a plant stock suffering from a seed-borne disease in a field where the disease has occurred, or its rhizospheric soil. When the plant tissue is used as a separation source, the tissue surface is preferably disinfected. The disinfection may be performed, for example, by soaking the collected plant tissue piece of about 1 cm$^2$ in 70% ethanol for 30 seconds and subsequently in 1% hypochlorous acid for 3 minutes to disinfect the tissue surface, followed by washing with sterile water. However, the concentration of ethanol or hypochlorous acid and the soaking time are not particularly limited and may be properly adjusted based on a known technique in the art depending on the site of the plant tissue and the like.

(2) Separation Method

When the biological control agent microbe is a true fungus, the surface-disinfected plant tissue is cut and divided into tissue pieces of about 1 cm$^2$ using sterilized tweezers, a surgical knife, or the like and placed on a culture medium. PSA (potato decoction agar medium: 200 g/L of potato decoction, 0.5% [w/v] sucrose, 1.5% [w/v] agar) or WA (plain agar medium: 1% agar) may be used as the culture medium. In addition, when the genus name of the biological control agent microbe to be separated is clear, a selection medium compatible with the genus may also be used. To prevent contamination with bacteria, 20% lactic acid is preferably applied onto the medium in advance. The culture medium on which the plant tissue was placed is cultured at 25 to 30° C. for 2 to 5 days. The single colonies (for a unicellular eukaryotic microbe), hyphal tips (for a filamentous fungus or a basidiomycete), spores, or conidia grown on a culture medium plate are retransferred to a fresh culture medium plate to establish a single colony strain.

Similarly, when the biological control agent microbe is a bacterium, the surface-disinfected plant tissue is cut and divided into tissue pieces of about 1 cm$^2$ using sterilized tweezers, a surgical knife, or the like and placed on a culture medium. PSA or King B medium (2% [w/v] peptone, 1% [w/v] glycerin, 0.15% [w/v] dipotassium hydrogen phosphate, 0.15% [w/v] magnesium sulfate heptahydrate, 1.5% [w/v] agar) may be used as the culture medium, and when the genus name of the biological control agent microbe to be separated is clear, a selection medium compatible with the genus may also be used. The culture medium on which the plant tissue was placed is cultured at 25 to 30° C. for 1 to 3 days. The generated single colony is scraped and transferred to a fresh culture medium plate to establish the regrown colony as a single strain.

(3) Separation of Non-Pathogenic Microbes

Whether or not a separated seed-borne pathogen is a non-pathogenic microbe, i.e., a biological control agent microbe to be used in the present invention, may be determined by infecting a seedling of a host plant with the microbe established as a strain in the above (2) and confirming the absence of characteristic disease symptoms in the seedling, for separation.

1-3. Constituents

The method for producing seeds of a plant resistant to seedling diseases according to the present invention comprises a contacting step and a collecting step. Each step will be specifically described below.

(1) Contacting Step

The "Contacting step" is a step of contacting a biological control agent microbe with a flower part of a host plant around the flowering time.

In this step, any of the biological control agent microbes is made to colonize in a host plant before a seed-borne pathogen infects the flower part of the host plant and colonizes in its seed.

As used herein, the "flowering time" is a period during which a host plant blooms. The "around the flowering time" refers to a period including before the commencement of flowering of a host plant and after the end of flowering. This period is a period including the flowering time as well as 2 weeks before and after, preferably 10 days before and after, more preferably 1 week or 5 days before and after the flowering time. For example, when the host plant is rice and the period is a period including the flowering time as well as 2 weeks before and after the flowering time, the period encompasses a period from the panicle growth stage in which the panicle of the rice grows rapidly until the flowering time of its stock is completed and the seeds matures.

As described above, the time when the biological control agent microbe is contacted with a flower part of a host plant is before the host plant is infected with a seed-borne pathogen which emerges or may emerge in a specific area. This is because that when the infection of the host plant with the seed-borne pathogen is before that with the biological control agent microbe, the effect of the present invention cannot be obtained since the action of eliminating infection with other microbes by the seed-borne pathogen (competitive action) precludes the infection of the host plant with the biological control agent microbe.

The type of the biological control agent microbe to be contacted is not particularly limited. Generally, the infection of an infected host plant with any biological control agent microbe makes difficult for other seed-borne pathogens to infect owing to occupation and competitive action by the biological control agent microbe and/or owing to resistance induced in the host plant by the infection of the biological control agent microbe. The present invention utilizes this principle, and the contact of a biological control agent microbe with a host plant can control subsequent infection with pathogens of seedling diseases including a seed-borne pathogen regardless of their microbial species. Hence, the seed of a host plant obtained by the present production method can be resistant to seedling diseases. Commonly, a non-pathogenic microbe may be used, which corresponds to a seed-borne pathogen which emerges or may emerge in an area where seeds of a plant resistant to a seedling disease are to be seeded. For example, in a field where rice bakanae disease occurs, a non-pathogenic fungus of the genus *Fusarium* corresponding to the rice bakanae disease fungus may be used as a biological control agent microbe. For example, *Fusarium oxysporum* strain W3 (Accession Number: NITE BP-01538) or *Fusarium oxysporum* strain W5 (Accession Number: NITE BP-01539) may be used, which is a non-pathogenic fungus in the genus *Fusarium*. Of course, from the above reason, a comparable effect can also be obtained even when a biological control agent microbe derived from a non-pathogenic fungus corresponding to another seed-borne pathogenic fungus is used. However, preferably, the biological control agent microbe to be contacted is not a mixture of a plurality of different strains but a single strain.

The number of contacts of a biological control agent microbe is not limited. For species in which the florets contained in the spicule blossom in succession, such as a gramineous plant, the step may be performed on several times in order to cause all flower parts to be thoroughly infected with the biological control agent microbe. However, the biological control agent microbe contacted on each time is preferably the same strain from the above reason.

The method for contacting a biological control agent microbe with a host plant is not particularly limited as long as that it enables contact of the biological control agent microbe. Examples thereof include methods, such as spraying, dispersing, applying, or soaking a culture solution, a suspension, a powder formulation, and the like of a biological control agent microbe described later. The place of a host plant to be contacted may be part or all of the host plant body; however, for a case that part of the plant body is contacted, it should be noted that a site associated with the infection route of a biological control agent microbe in the host plant, i.e., the flower part, is contacted.

(2) Collecting Step

The "collecting step" is a step of collecting seed(s) of the host plant colonized by the biological control agent microbe obtained after the above contact step. The biological control agent microbe contacted with the flower part of the host plant in the contact step typically colonizes in the glume, seed coat, or ovule tissue. The host plant develops seed(s) colonized by a non-pathogenic mutant strain after pollination. Thus, in this step, seed(s) having matured sufficiently to have a germination capacity may be collected by a method known in the art. The seed obtained from the host plant after the contacting step can be regarded, in principle, as a seed of a plant resistant to seedling diseases.

After the collecting step, if necessary, the seeds may be dried in order to improve their storage stability. The method of drying may be any method provided that it is a method which involves properly decreasing water in the seeds while retaining the germinability of the seeds without causing the death of the colonized biological control agent microbe. Examples thereof include an natural drying method involving exposure to the air, a dehumidification drying method involving placement in a sealed container with a dehumidifying agent, an air drying method involving drying by sending warm air or cold blast using a blower or the like, and a combination thereof. The subsequent storage method for the seeds may be according to a method well-known in the art.

If necessary, it may also be confirmed whether or not the seeds after the collecting step are microbe-carrying seeds colonized by the biological control agent microbe. That may be readily confirmed by preparing nucleic acid from a portion or all of microbe-carrying seed candidates and then using the technique based on a nucleic acid amplification method such as PCR with nucleotide sequences specific to the gene of the contacted biological control agent microbe designed as primers. For example, when the biological control agent microbe is *Fusarium oxysporum*, the IGS region of ribosomal DNA may be a specific nucleotide sequence enabling the identification of the presence of the biological control agent microbe. Hence, the region may be used as a primer set for amplification. Specific examples thereof include FIGS11 (5'-GTAAGCCGTCCTTCGC-CTCG-3': SEQ ID NO: 1) and FIGS12 (5'-GCAAAAT-TCAATAGTATGGC-3': SEQ ID NO: 2). The use of the primer set amplifies a DNA fragment having the nucleotide sequence set forth in SEQ ID NO: 3 for *Fusarium oxysporum* strain W3 (Accession Number: NITE BP-01538) and a DNA fragment having the nucleotide sequence set forth in SEQ ID NO: 4 for *Fusarium oxysporum* strain W5 (Accession Number: NITE BP-01539). Thus, which strains of the biological control agent microbe derived from *Fusarium oxysporum* colonizes can be confirmed and identified.

A seedling individual of the resultant plant resistant to seedling diseases can grow as a stock resistant to seedling diseases without showing disease symptoms by the competitive action of the biological control agent microbe since the seed carries the biological control agent microbe.

1-4. Effect

The method for producing seeds of a plant resistant to seedling diseases according to the present invention enables the simple production and provision of a seed of a plant resistant to any seedling diseases as though the seedling individual is a variety resistant to seedling diseases.

Since the method for producing seeds of a plant resistant to seedling diseases according to the present invention is needed to be performed for at least a plant for collecting seeds only, the method enables limiting the area for applying a biological control agent microbe to the minimum and therefore little affects the environment and is also economically excellent.

The seed of a plant resistant to seedling diseases according to the present invention eliminates the need for applying treatment for controlling or suppressing the onset of seed-borne diseases to a seed before seeding and enables the cultivation of a host plant not having the onset of seedling diseases only by usual seeding, and thus enables reduction of labor and cost. The seed also eliminates the need for, or enables the reduction of, seed disinfection with a chemical pesticide.

The method for producing seeds of a plant resistant to seedling diseases according to the present invention is highly safe and affects the environment little compared to that using a chemical pesticide since it uses a microbial pesticide utilizing a non-pathogenic microbe present in nature.

2. Method for Preventing Onset of and Controlling Seedling Disease

A second aspect of the present invention relates to a method for preventing the onset of and controlling seedling diseases. The present invention can prevent the onset of and controlling seedling diseases in a seedling individual resistant to seedling diseases and other plant individuals around the seedling individual.

2-1. Constituents

The method for preventing onset of and controlling the seedling diseases according to the present invention (hereinafter, often referred to as the "prevention and control method") uses the seed of a plant resistant to seedling diseases described in the first aspect, colonized by a biological control agent microbe. The fundamental process of the prevention and control method of the present invention is only performing a typical cultivation method for the species of a plant resistant to seedling diseases. However, seed disinfection prior to seeding does not need to be carried out.

Taking rice as an example, seed paddies of rice resistant to seedling diseases are made to sprout and seeded in a container containing culture soil (a seedling box or the like) for raising seedling. Thereafter, it suffices to set the seedlings in a field followed by cultivation using a conventional method.

The seed of a plant resistant to seedling diseases described in the first aspect is colonized by a biological control agent microbe. However, the biological control agent microbe is non-pathogenic and thus does not cause the onset of seedling diseases. Thus, the seedling enables efficient prevention and control of infection with a pathogen of seedling diseases including seed-borne diseases and soil-borne diseases.

In addition, the biological control agent microbe colonizing in the seed of a plant resistant to seedling diseases retains infectivity although it is non-pathogenic, and thus, when the seed of a plant resistant to seedling diseases is cultivated together with seeds not infected with a seed-borne pathogen, it can be transmitted to the surrounding healthy seedlings in the seed soaking to seedling raising period. However, that results in the occupation of the biological control agent microbe and the pathogen resistance induced in the plant itself infected therewith, and enables the efficient prevention and control of subsequent infection with a pathogen of seedling diseases including seed-borne diseases and soil-borne diseases.

2-2. Effect

The prevention and control method of the present invention enables efficient prevention and control of seedling diseases including seed-borne diseases and soil-borne diseases without special treatment.

The prevention and control method of the present invention enables reduction of labor and cost, since it makes the seed disinfection conventionally performed before seeding unnecessary.

The prevention and control method of the present invention enables efficient prevention and control of infection with a pathogen of seedling diseases including seed-borne diseases and soil-borne diseases in not only a seedling individual of a plant resistant to seedling diseases described in the first aspect but also healthy individuals cultivated together therewith.

3. Microbial Pesticide for Controlling Seedling Disease

A third aspect of the present invention relates to a microbial pesticide for controlling seedling diseases. The microbial pesticide for controlling seedling diseases according to the present invention maybe applied to a desired plant to impart resistance to seedling diseases to the plant.

3-1. Constituents

The microbial pesticide for controlling seedling diseases according to the present invention contains a biological control agent microbe as an active ingredient.

The biological control agent microbe may be the biological control agent microbe described in the first aspect. Specific examples of the biological control agent microbe include a non-pathogenic fungus, *Fusarium oxysporum* strain W3 (Accession Number: NITE BP-01538) or *Fusarium oxysporum* strain W5 (Accession Number: NITE BP-01539), as a species closely-related to *Fusarium fujikuroi* causing the onset of rice bakanae disease. In order to achieve the effects of the present invention, it is necessary for the biological control agent microbe to maintain colonizing ability in a host plant. Thus, the biological control agent microbe in the microbial pesticide of the present invention must be maintained in a live state.

The amount of the biological control agent microbe per dose of the microbial pesticide for controlling seedling diseases according to the present invention depends on conditions, such as the type thereof, the type of the application target plant, the dosage form, and the application (contact) method. Generally, it is preferable that biological control agent microbe as an active ingredient is contained in an amount sufficient for contact with and colonization in an application target plant, when the microbial pesticide of the present invention is applied. The content of the biological control agent microbe may be determined, considering the conditions so that the amount of the biological control agent microbe contained in the microbial pesticide of the present invention is a desired amount for a target plant after application based on common technical knowledge in the art. For example, when the biological control agent microbe is derived from the genus *Fusarium* and the microbial pesticide of the present invention is in a liquid state, conidia thereof may be contained in an amount of $1.0 \times 10^4$/mL or more, preferably $5.0 \times 10^4$/mL or more in the solution. The upper limit is not particularly limited; however, $1.0 \times 10^9$/mL or so will be usually sufficient even for a biological control agent microbe having a low infection rate.

The microbial pesticide of the present invention may contain a carrier acceptable to pesticide formulation in the range not inhibiting or suppressing the host plant-infecting activity of a biological control agent microbe.

The "carrier acceptable to pesticide formulation" refers to a substance facilitating the application of a microbial pesticide, maintaining the viability and infectivity of a biological control agent microbe as an active ingredient and/or controlling the speed of action of the microbial pesticide, wherein the substance has no or little deleterious effects on the environment such as soil and water quality, or has no or low harmful effects on animals, particularly humans when applied to the outdoor and indoor cultivation of a plant. Examples thereof include an excipient. Preferred examples of the excipient include pulverized natural minerals, pulverized synthetic minerals, emulsifiers, dispersants, surfactants, and the like.

Examples of the pulverized natural minerals include, for example, kaolin, clay, talc, and chalk.

Examples of the pulverized synthetic minerals include, for example, highly dispersible silica and silicate. Examples of the emulsifiers include non-ionic emulsifiers and anionic emulsifiers (for example, polyoxyethylene fatty alcohol ethers, alkyl sulfonates, and aryl sulfonates).

Examples of the dispersants include, for example, ligninsulfite waste liquors and methylcellulose.

Examples of the surfactants include lignosulfonic acid, naphthalenesulfonic acid, phenolsulfonic acid, alkali metal, alkaline earth metal, and ammonium salts of dibutylnaphthalenesulfonic acid, alkylarylsulfonates, alkylsulfates, alkylsulfonates, fatty alcohol sulfates, fatty acid and sulfated fatty alcohol glycol ethers, condensates of sulfonated naphthalene and naphthalene derivatives with formaldehyde, condensates of naphthalene or naphthalenesulfonic acid with phenol and formaldehyde, polyoxyethylene octylphenylether, ethoxylated isooctyl phenol, octyl phenol, nonyl phenol, alkylphenyl polyglycol ethers, tributylphenyl polyglycol ethers, tristearylphenyl polyglycol ethers, alkylaryl polyether alcohols, condensates of alcohol and fatty alcohol/ethylene oxide, ethoxylated castor oil, polyoxyethylene alkyl ethers, ethoxylated polyoxypropylenes, lauryl alcohol polyglycol ether acetal, sorbitol esters, lignin-sulfite waste liquors, and methylcellulose.

The microbial pesticide of the present invention can contain one or more carriers acceptable to pesticide formulation described above. It can further contain active ingredients having other pharmacological actions, i.e., a herbicide, a fungicide, an insecticide, and a fertilizer (e.g., urea, ammonium nitrate, or a superphosphate) in the range not affecting infection of a biological control agent microbe.

The dosage form of the microbial pesticide of the present invention may have any state provided that the colonizing ability of a biological control agent microbe in a host plant can be retained in the state, and, for example, it may have a liquid state in which the biological control agent microbe is suspended in a suitable solution, a solid state (including a powder state), or a combination thereof. The liquid state needs only to be one in which a biological control agent microbe as an active ingredient is suspended in a suitable solution. Examples of the suitable solution include water, buffer, and a culture medium for the biological control agent microbe. The solid state is not particularly limited provided that a biological control agent microbe as an active ingredient can act on a host plant in the state. Examples thereof include a granule state, a powder state, and a state of semisolid such as gel. In view of the fact that the microbe adheres to a host plant by contact or the like, proliferates, and acts, the state is preferably a powder state (particularly, a state of powder having adhesiveness) or a gel state.

3-2. Effect

The microbial pesticide for controlling seedling diseases according to the present invention can provide an inexpensive and efficient agent for simply producing a plant resistant to seedling diseases or for preventing the infection of a host plant.

EXAMPLES

The Examples of the present invention will be described below with reference to specific examples. However, the present invention is not limited to the embodiments of the Examples.

Example 1

Effect of Controlling Seedling Disease in Plant Resistant to Seedling Disease (1)

(Purpose)

Microbial pesticides for controlling seedling diseases according to the present invention were prepared; seeds were prepared by the method for producing seeds of a plant resistant to seedling diseases using the microbial pesticides; and it was verified on a pot scale that seedling individuals were resistant to seedling diseases.

(Material and Method)

Non-pathogenic fungi, *Fusarium oxysporum* strains W3 (Accession Number: NITE BP-01538) and W5 (Accession Number: NITE BP-01539) were used as the biological control agent microbes.

Each of the biological control agent microbes was subjected to shaking culture at 28° C. for 5 days in PSB (potato decoction) medium (200 g/L of potato decoction, 0.5% [w/v] saccharose). Conidia in the culture solution were collected by centrifugation (1,500×g, 20 minutes), and a spore suspension diluted to $1.0 \times 10^5$ to $1.0 \times 10^7$/mL with sterile water was used as a microbial pesticide for controlling seedling diseases.

The host plant used was rice (variety: Tangin-bozu). After placing 80 g of sterile culture soil as bed soil in a 200-mL plastic pot followed by watering, 2 seeds of rice were seeded as parent rice seeds, covered by 20 g of sterile culture soil, and again watered. After seeding, cultivation was performed in an artificial meteorological room set at 26° C. under conditions of natural light for 100 days.

The method for contacting each of the microbial pesticides with the parent rice involved, 1 week after the first flowering of the parent rice, directly spraying the microbial pesticide on the flower part using a hand spray at a certain time during the morning (around 10 to 11 o'clock) when the rice flowers (contacting step). The amount of spray was about 5 mL per spica. The spray-treated parent rice was cultivated in an artificial meteorological room set at 26° C. under conditions of natural light until the seeds ripen. About the time when the terrestrial part of the parent rice turns yellow, it was threshed to collect seed paddies (collecting step). The seed paddies collected in the treatment are hereinafter referred to as the "W3-treated seed paddies" and "W5-treated seed paddies" (corresponding to seeds of a plant resistant to seedling diseases according to the present invention). On the other hand, control seed paddies collected by the same operation except for spraying sterile water in place of the microbial pesticide are hereinafter referred to as the "untreated seed paddies". Each of the treated seed paddies and the untreated seed paddies were each dried before germination treatment.

The respective seed paddies were soaked in a suspension of spores of pathogenic *Fusarium fujikuroi* as a causative fungus of rice bakanae disease ($1.0 \times 10^3$/mL, preparation method was the same as that for the suspension of spores of biological control agent microbes) at a bath ratio of 1:1 for soaking treatment at 15° C. for 4 days. Then, forced sprouting treatment was carried out at 30° C. for 1 day. After placing 80 g of sterile culture soil as bed soil in a 200-mL plastic pot followed by watering, the respective treated seed paddies and the untreated seed paddies were seeded in the pot, covered by 20 g of sterile culture soil, and again watered. The amount of seed paddies per pot was about 2 g (about 70 grains) by dry weight before soaking treatment. Pots in which the W3-treated seed paddies, the W5-treated seed paddies, and the untreated seed paddies were seeded were referred to as a W3 treatment zone, a W5 treatment zone, and an untreatment zone, respectively. After seeding, cultivation was performed in an artificial meteorological room set at 28° C. under conditions of natural light for 14 days, and the effect of the present invention was tested by comparing rice growth in the pots.

In disease symptom evaluation, a stock in which spindly growth of plant length and yellowing were observed was defined as a seedling with rice bakanae disease, and the rice bakanae disease infection rate of seedlings and the control effect were calculated using the following equations.

Infection Rate of Seedlings (%)=Number of Diseased Seedlings/Total Number of Seedlings×100

Control effect=(Infection Rate of Seedlings in Untreatment−Infection Rate of Seedlings in Treatment)/Infection Rate of Seedlings in Untreatment×100

There was no significant difference in the germination rate between the treatment zones, in which the rates were roughly 90% or more.

(Results)

The results are shown in Table 1.

TABLE 1

| Treatment | Infection Rate of Seedling (%) | Control effect |
| --- | --- | --- |
| Untreatment | 30.50 | — |
| W3 Treatment | 3.91 | 87.2 |
| W5 Treatment | 4.29 | 85.9 |

As shown in Table 1, about 30.5% of rice seedling had the onset of rice bakanae disease in the untreatment zone as a negative control, while the infection rates of seedlings in rice seedling in the W3 and W5 treatment zones where the seeds of rice resistant to seedling diseases were seeded were each less than 5%. This demonstrated that the seeds obtained by the method for producing a seed of a plant resistant to seedling diseases using the microbial pesticide of the present invention acquired extremely high resistance to seedling diseases. Since the seed of rice resistant to seedling diseases obtained by treatment with a non-pathogenic fungus of *Fusarium oxysporum*, strain W3 or W5, showed resistance to rice bakanae disease caused by *Fusarium fijikuroi* belonging to the different species, it was shown that the seed of rice resistant to seedling diseases obtained by treatment with each biological control agent microbe and colonization by the microbe also provided high preventive and control activities against seedling disease caused by a pathogenic fungus belonging to species other than that of the biological control agent microbe.

Example 2

Effect of Controlling Seedling Disease in Plant Resistant to Seedling Disease (2)

(Purpose)

A microbial pesticide for controlling seedling diseases according to the present invention was prepared; seeds were prepared by the method for producing a seed of a plant resistant to seedling diseases using the microbial pesticide; and it was verified on a field scale that seedling individuals were resistant to seedling diseases.

(Material and Method)

Non-pathogenic fungus, *Fusarium oxysporum* strain W5 (Accession Number: NITE BP-01539) was used as the microbial pesticide for controlling seedling diseases, according to Example 1. The concentration of conidia in the culture solution was $1.0 \times 10^5$/mL.

Rice (variety: Tangin-bozu) was used as a host plant and cultivated by the following method for contact with the non-pathogenic fungus. The basic operation is according to Example 1. Seed paddies of the parent rice were first soaked in a disinfectant consisting of a 1:200 diluted solution of 250 mg/L of ipconazole/230 mg/L of wettable powder of copper hydroxide to disinfect the seeds. The resultant disinfection-treated parent rice seed paddies were subjected to raising seedling according to a known method (conventional method) in the art. No Rice bakanae disease control was carried out except treatment with the above disinfectant.

Rice (variety: Koshihikari) naturally-infected with rice bakanae disease was used as a source of rice bakanae disease infection in the field. Seed paddies of the infection source were subjected to raising seedling without seed disinfection.

Both seedlings were set in the major field at the 32nd day after seeding before onset.

The non-pathogenic fungus of the present invention was contacted with the parent rice by directly spraying the non-pathogenic fungus on the flower part using a hand spray at a certain time during the morning (around 10 to 11 o'clock) when the parent rice flowers on two times, i.e., at heading stage at the 88th day after setting, at which the heading rate reaches 40 to 50% and at full heading stage at the 91st day after setting at which the heading rate reaches 80 to 90%. The amount of spray was about 140 mL/m$^2$. The spray-treated parent rice was cultivated according to a conventional method. At the 155th day after setting the parent rice, rice was reaped and threshed to collect seed paddies.

The rice bakanae disease infection rate was verified for the obtained seed paddies. The basic operation was according to Example 1. However, in this Example, since natural infection from bakanae disease-infected Koshihikari in the field was used as a pollution source, it was not necessary in principle to inoculate seed paddies with the pathogenic fungus. Thus, only the soaking treatment of seed paddies was performed using sterile water in place of the rice bakanae disease fungus spore suspension and the effect of suppressing disease onset was tested according to Example 1. In disease symptom evaluation, a stock in which spindly growth of plant length and yellowing were observed was defined as a diseased seedling, and the disease infection rate of seedlings and the control effect were calculated using the equations described in Example 1.

(Results)

The results are shown in Table 2.

TABLE 2

| Treatment | Infection Rate of Seedling (%) | Control effect |
|---|---|---|
| Untreatment | 89.76 | — |
| W3 Treatment | 29.38 | 67.3 |
| W5 Treatment | 6.59 | 92.7 |

As shown in Table 2, the rice bakanae disease infection rate of seedlings in the rice seedling in the non-pathogenic fungus W3 treatment zone or W5 treatment zone where seeds of rice resistant to seedling diseases were seeded remained at about 30% with the control effect being more than 65% for the W3 treatment zone, and was only about 6.6% with the control effect being more than 90% for the W5 treatment zone. This experiment demonstrated the effect of the present invention even on a field scale.

Example 3

Effect of Controlling Seedling Disease in Plant Resistant to Seedling Disease (3)

(Purpose)

It was verified that seedling individuals of plants resistant to seedling diseases according to the present invention was resistant to seedling diseases by inoculating a pathogenic fungus under more severe conditions than those for Example 2.

(Material and Method)

The materials and the basic operation were according to Examples 1 and 2. However, in this Example, treatment with a non-pathogenic fungus was carried out in a field and seed paddies were prepared using natural infection from bakanae disease-infected Koshihikari as a pollution source as in Example 2, but in forced sprouting treatment, seed paddies were additionally inoculated with the pathogenic fungus by soaking not in sterile water but in a suspension of spores of a rice bakanae disease fungus, *Fusarium fujikuroi* under the same conditions as those in Example 1. This is an control test carried out supposing that some seeds polluted with the bakanae disease fungus remain and that bakanae disease spread to adjacent stocks in raising seedling.

(Results)

The results are shown in Table 3.

TABLE 3

| Treatment | Infection Rate of Seedling (%) | Control effect |
|---|---|---|
| Untreatment | 52.33 | — |
| W3 Treatment | 19.88 | 62.0 |
| W5 Treatment | 14.29 | 72.7 |

In spite of the fact that treatment under more severe onset conditions was performed by inoculation with spores of the rice bakanae disease fungus in the form of a suspension in addition to the same natural infection as that in Example 2, the rice bakanae disease infection rate of seedlings was about 20% with the control effect being 62% in the non-pathogenic fungus W3 treatment zone, and the rice bakanae disease infection rate of seedlings was about 15% with the control effect being more than 70% in the non-pathogenic fungus W5 treatment zone. Thus, the effect of the present invention was demonstrated regardless of the difference in severity of infection conditions of seedling disease fungus.

Example 4

Effect of Controlling Seedling Disease in Plant Resistant to Seedling Disease (4)

(Purpose)

It was verified on a pot scale using a fungal strain of the genus *Trichoderma* that seedling individuals of plants resistant to seedling diseases according to the present invention became resistant to seedling diseases even when a fungal strain other than a fungus of the genus *Fusarium* was used.

(Material and Method)

The materials and the basic operation were according to Example 1. However, in this Example, *Trichoderma atrovidide* strain SKT-1 commercially available as a microbial pesticide (product name: Ecohope, Kumiai Chemical Industry Co., Ltd.) was used together with a non-pathogenic fungus, *Fusarium oxysporum* strain W5. Conidia were used by scraping the ones formed not in liquid culture but in plate culture. The concentration of conidia was $1.0 \times 10^5$/mL, and spray on the flower part was carried out 4 times in total every 2 days from the 87th day after setting.

(Results)

The results are shown in Table 4.

TABLE 4

| Treatment | Infection Rate of Seedling (%) | Control effect |
|---|---|---|
| Untreatment | 13.0 | — |
| W5 Treatment | 1.8 | 86.5 |
| Trichoderma Treatment | 6.0 | 53.6 |

As shown in Table 4, in the Trichoderma fungus treatment zone, the disease infection rate of seedlings remained at about 6.0% with the control effect being more than 50%. This experiment demonstrated the effect of the present invention not only when a non-pathogenic fungus Fusarium oxysporum, strain W3 or W5, was used but also when a fungus of the genus Trichoderma was used. Thus, it is considered that the present invention can be practiced using a wide range of fungi including fungi of the genus Fusarium and the genus Trichoderma.

All publications, patents, and patent applications cited in this application are incorporated herein by reference in their entirety.

The invention claimed is:

1. A method for producing seeds of a plant resistant to seedling diseases, comprising the steps of:

(a) contacting a separated non-pathogenic microbe with a flower part of a host plant around the flowering time, wherein the separated non-pathogenic microbe is applied in an amount sufficient for contact with and colonization in the host plant to control subsequent infection with a seed-borne pathogen, wherein the separated non-pathogenic microbe belongs to the same species or the same genus as the seed-borne pathogen; and (b) collecting seeds of the host plant colonized by the non-pathogenic microbe, obtained after step (a), wherein the separated non-pathogenic microbe is *Fusarium oxysporum* non-pathogenic strain W3 Accession Number NITE BP-01538 or *Fusarium oxysporum* non-pathogenic strain W5 Accession Number NITE BP-01539.

2. The production method according to claim 1, wherein the host plant is a gramineous plant.

3. The production method according to claim 2, wherein the gramineous plant is rice.

4. The production method according to claim 1, wherein the separated non-pathogenic microbe is in a liquid state comprising $1\times10^4$ conidia, or more.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: synthetic

<400> SEQUENCE: 1
gtaagccgtc cttcgcctcg                                               20

<210> SEQ ID NO 2
<211> LENGTH: 20
<212> TYPE: DNA
<213> ORGANISM: Artificial
<220> FEATURE:
<223> OTHER INFORMATION: synthetic

<400> SEQUENCE: 2
gcaaaattca atagtatggc                                               20

<210> SEQ ID NO 3
<211> LENGTH: 619
<212> TYPE: DNA
<213> ORGANISM: Artificial
<220> FEATURE:
<223> OTHER INFORMATION: synthetic

<400> SEQUENCE: 3
atttccccaa tgggttctcc ggatttctgg agacttgtag gggttgtggg tatttcgatg    60
tgtcgtctcc ggacgggcgg tgcagggtag tcgagttgga cttggtggaa ttcggtttat   120
tcgaatccgt cgagtctggc tggcacgatc gtgtgcggct gtgtgctgga cggtgtaggg   180
taggctgctt ggacatggtc ggttcgagga tcgattcgag ggccggcctc tcgatgatgt   240
gtgatgtatg cggtctaggg taggctggtt tgtcttggtc caatttgatg tcggctcccg   300
tgcagaccag agtgagtgtg gtccagggta ggtccagggt aggcagctta gatttgatcg   360
atctggaggt cgattctccg ggctggcgga tctgacactg tcgaaacgag atgcgagcgg   420
tgtagggtag gccagttttg tcgtcgccag gttgcgattc ggacgagata tgtggtctag   480
ggtaggccct agggtaagta gagttcgagt ttcgtcgcca acagtttgct gtatgtgtag   540
ggtaggtgca gggtaagcaa atctctctct ggccagacgg ttttgcggtc tggtggtcgt   600
gagtcgattt ttttgtttt                                              619

<210> SEQ ID NO 4
<211> LENGTH: 618
<212> TYPE: DNA
<213> ORGANISM: Artificial
```

-continued

```
<220> FEATURE:
<223> OTHER INFORMATION: synthetic

<400> SEQUENCE: 4
atttccccaa tgggttctcc ggatttctgg agacttgtag gggttgtggg tttttcgatg      60
tgtcgtctcc ggacgggcgg tgcagggtag tcgagttgga cttggtggaa ttcggtttat     120
tcgaatccgt cgagtctggc tggcacgatc gtgtgcggct gtgtgctgga cggtgtaggg     180
taggctgctt ggacatggtc ggttcgagga tcgattcgag ggccggcctg tcgatgatgt     240
gtgatgtatg cggtctaggg taggctggtt tgtcttggtc caatttgatg tcggctcccg     300
tgcagaccag agtgagggcg gtccagggta ggtccagggt aggcagctta gatttgatcg     360
atctggaggt cgattctccg gctggcggat ctgacactgt cgaaacgaga tgcgagcggt     420
gtagggtagg ccagttttgt cgtcgccagg ttgcgattcg gacgagatat gtggtctagg     480
gtagggtcta gggtaagtag agttcgagtt tcgtcgccaa cagtttgctg tatgtgtagg     540
gtaggtgcag ggtaagcaaa tctctctctg gccagacggt tttgcggtct ggtggttgtg     600
agtcgatttt tttgtttt                                                   618
```